US008973293B2

(12) United States Patent
Palmer et al.

(10) Patent No.: US 8,973,293 B2
(45) Date of Patent: Mar. 10, 2015

(54) SPECIMEN CONTAINER LABEL FOR AUTOMATED CLINICAL LABORATORY PROCESSING SYSTEMS

(75) Inventors: Ashley Palmer, Philadelphia, PA (US); Robert S. Ross, Hacienda Heights, CA (US); Paul Holmes, New York, NY (US); Robert S. Golabek, Jr., Towaco, NJ (US); Shenika E. Felix, Hewitt, NJ (US); Nancy Dubrowny, Garfield, NJ (US); Kristine Conley, North Haledon, NJ (US); Christine Bush, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/295,251

(22) Filed: Nov. 14, 2011

(65) Prior Publication Data
US 2012/0210778 A1  Aug. 23, 2012

Related U.S. Application Data

(60) Provisional application No. 61/415,665, filed on Nov. 19, 2010.

(51) Int. Cl.
*G09F 3/10* (2006.01)
*B01L 3/00* (2006.01)
*A61B 6/00* (2006.01)
*G01N 35/00* (2006.01)

(52) U.S. Cl.
CPC ............ *B01L 3/5453* (2013.01); *A61B 6/5294* (2013.01); *G09F 3/10* (2013.01); *B01L 3/5082* (2013.01); *B01L 2300/021* (2013.01); *B01L 2300/0832* (2013.01); *G01N 2035/00861* (2013.01)

USPC .......................................................... 40/638

(58) Field of Classification Search
CPC ............... A61B 6/5294; A61B 8/5292; G01N 2035/00861; B01L 3/5453
See application file for complete search history.

(56) References Cited

U.S. PATENT DOCUMENTS

| 3,266,298 A | 8/1966 | Whitehead et al. |
| 3,482,082 A | 12/1969 | Isreeli |
| 3,553,041 A | 1/1971 | Von Hofe |

(Continued)

FOREIGN PATENT DOCUMENTS

| EP | 510615 A1 | 10/1992 |
| EP | 0486059 B1 | 1/1997 |

(Continued)

*Primary Examiner* — Kristina Junge
(74) *Attorney, Agent, or Firm* — The Webb Law Firm

(57) ABSTRACT

A label and labeling system for identifying the volume of a specimen within a specimen collection container are disclosed. The system includes providing a specimen collection container having an open top end, a closed bottom end, and a sidewall extending therebetween forming an interior adapted for receiving a specimen therein. The specimen collection container also includes a label having a label body disposed over at least a portion of the sidewall, in visual alignment with a colored background. At least one of the sidewall of the specimen collection container and the label body have printing disposed thereon having a color that is substantially identical to the colored background against which the specimen collection container will be viewed. At least one of the sidewall of the specimen collection container and the label body may have colorless indicia having a surface enhancement feature for providing visual distinction.

29 Claims, 13 Drawing Sheets

(56) References Cited

U.S. PATENT DOCUMENTS

| | | |
|---|---|---|
| 3,619,568 A | 11/1971 | Taplin |
| 3,653,176 A | 4/1972 | Gess |
| 3,656,473 A | 4/1972 | Sodickson et al. |
| 3,843,440 A | 10/1974 | Davies |
| 3,898,433 A | 8/1975 | Sallet |
| 3,985,605 A | 10/1976 | Treiber et al. |
| 4,015,352 A | 4/1977 | Prange |
| 4,122,947 A | 10/1978 | Falla |
| 4,292,916 A | 10/1981 | Bradley et al. |
| 4,344,994 A | 8/1982 | Batty et al. |
| 4,397,318 A | 8/1983 | Burns |
| 4,411,163 A | 10/1983 | White |
| 4,480,470 A | 11/1984 | Tussing |
| 4,576,185 A | 3/1986 | Proud et al. |
| 4,589,141 A | 5/1986 | Christian et al. |
| D285,115 S | 8/1986 | Proud et al. |
| 4,626,314 A | 12/1986 | Wesley |
| 4,646,753 A | 3/1987 | Nugent |
| 4,654,127 A | 3/1987 | Baker et al. |
| 4,690,153 A | 9/1987 | Losada et al. |
| 4,763,930 A * | 8/1988 | Matney .......... 283/81 |
| 4,828,716 A | 5/1989 | McEwen et al. |
| 4,873,193 A | 10/1989 | Jensen et al. |
| 4,964,413 A | 10/1990 | Losada et al. |
| 4,967,763 A | 11/1990 | Nugent et al. |
| 5,025,798 A | 6/1991 | Schindele |
| 5,038,794 A | 8/1991 | Van Valkenburg |
| 5,061,263 A | 10/1991 | Yamazaki et al. |
| 5,143,084 A | 9/1992 | Macemon et al. |
| 5,150,795 A | 9/1992 | Nakayama |
| 5,164,575 A | 11/1992 | Neeley et al. |
| 5,220,302 A | 6/1993 | Nunnally et al. |
| 5,288,466 A | 2/1994 | Burns |
| 5,384,096 A | 1/1995 | Burns |
| D356,643 S | 3/1995 | Burns |
| 5,401,110 A | 3/1995 | Neeley |
| D357,985 S | 5/1995 | Burns |
| 5,458,113 A | 10/1995 | Burns |
| 5,458,854 A | 10/1995 | Burns |
| 5,494,170 A | 2/1996 | Burns |
| 5,527,513 A | 6/1996 | Burns |
| 5,552,117 A | 9/1996 | Burns |
| 5,633,835 A | 5/1997 | Haas et al. |
| 5,672,321 A | 9/1997 | Daykin |
| 5,688,361 A | 11/1997 | Itoh |
| 5,699,923 A | 12/1997 | Burns |
| 5,711,875 A | 1/1998 | Kayal et al. |
| 5,738,233 A | 4/1998 | Burns |
| 5,743,861 A | 4/1998 | Columbus et al. |
| 5,793,030 A | 8/1998 | Kelly, Jr. |
| 5,971,941 A | 10/1999 | Simons et al. |
| 6,017,318 A | 1/2000 | Gauthier et al. |
| 6,030,582 A | 2/2000 | Levy |
| 6,035,568 A | 3/2000 | Grosskopf et al. |
| D425,625 S | 5/2000 | Niermann |
| 6,056,925 A | 5/2000 | Sarstedt |
| 6,209,921 B1 | 4/2001 | Hogan et al. |
| 6,221,655 B1 | 4/2001 | Fung et al. |
| 6,279,759 B1 | 8/2001 | Weisbach |
| 6,335,692 B1 | 1/2002 | Compton |
| 6,358,476 B1 | 3/2002 | Innamorato et al. |
| 6,373,786 B1 | 4/2002 | Kagan et al. |
| 6,391,262 B1 | 5/2002 | Brinton et al. |
| 6,426,049 B1 | 7/2002 | Rosen et al. |
| 6,428,640 B1 | 8/2002 | Stevens et al. |
| 6,533,015 B1 | 3/2003 | Moore |
| 6,551,267 B1 | 4/2003 | Cohen et al. |
| 6,562,300 B2 | 5/2003 | Rosen et al. |
| 6,808,574 B1 | 10/2004 | Stevens et al. |
| 6,891,182 B2 * | 5/2005 | Watari et al. .......... 250/559.19 |
| 7,499,581 B2 * | 3/2009 | Tribble et al. .......... 382/141 |
| D640,797 S | 6/2011 | Wilkinson |
| D645,972 S | 9/2011 | Wilkinson |
| 2002/0154809 A1 * | 10/2002 | Yamagishi et al. .......... 382/142 |
| 2002/0156439 A1 | 10/2002 | Iskra |
| 2003/0235119 A1 | 12/2003 | Wien et al. |
| 2004/0171168 A1 | 9/2004 | Itoh |
| 2004/0176704 A1 | 9/2004 | Stevens |
| 2004/0200558 A1 | 10/2004 | Stevens et al. |
| 2004/0257918 A1 | 12/2004 | Ribi |
| 2006/0091669 A1 | 5/2006 | Wilkinson |
| 2006/0222802 A1 | 10/2006 | Stevens et al. |
| 2006/0249582 A1 | 11/2006 | Golabek et al. |
| 2007/0092585 A1 | 4/2007 | Skinner |
| 2008/0125673 A1 * | 5/2008 | Carano et al. .......... 600/584 |
| 2009/0193696 A1 | 8/2009 | Golabek et al. |
| 2010/0021343 A1 * | 1/2010 | Ostgaard et al. .......... 422/64 |
| 2010/0067024 A1 | 3/2010 | Swenson et al. |
| 2011/0178424 A1 * | 7/2011 | Wilkinson et al. .......... 600/573 |

FOREIGN PATENT DOCUMENTS

| | | |
|---|---|---|
| EP | 0992287 A2 | 4/2000 |
| EP | 1004359 A2 | 5/2000 |
| JP | 56092262 U | 7/1981 |
| JP | 1-156667 A | 6/1989 |
| JP | 3041365 A | 2/1991 |
| JP | 03-063570 A | 3/1991 |
| JP | 4-63484 U | 5/1992 |
| JP | 05-095936 A | 4/1993 |
| JP | 5097133 A | 4/1993 |
| JP | 5143794 A | 6/1993 |
| JP | 5-71792 U | 9/1993 |
| JP | 6-59937 | 8/1994 |
| JP | 07-167716 A | 7/1995 |
| JP | 8166765 A | 6/1996 |
| JP | 9-504608 A | 5/1997 |
| JP | 09133687 | 5/1997 |
| JP | 9-236608 A | 9/1997 |
| JP | 3048980 U | 5/1998 |
| JP | 2002-82120 A | 3/2002 |
| JP | 2002-102210 A | 4/2002 |
| JP | 2002-243734 A | 8/2002 |
| JP | 2003-004875 A | 1/2003 |
| JP | 2004-121704 A | 4/2004 |
| JP | 2004-347376 A | 12/2004 |
| JP | 2005249762 | 9/2005 |
| JP | 2006106455 | 4/2006 |
| WO | 01/26993 A1 | 4/2001 |
| WO | 02/06904 A1 | 1/2002 |
| WO | 2005/116632 A2 | 12/2005 |
| WO | 2007/092585 A2 | 8/2007 |
| WO | WO 2007092585 A2 * | 8/2007 |
| WO | 2008/031036 A1 | 3/2008 |
| WO | 2008078808 A1 | 7/2008 |
| WO | 2009111622 A2 | 9/2009 |

* cited by examiner

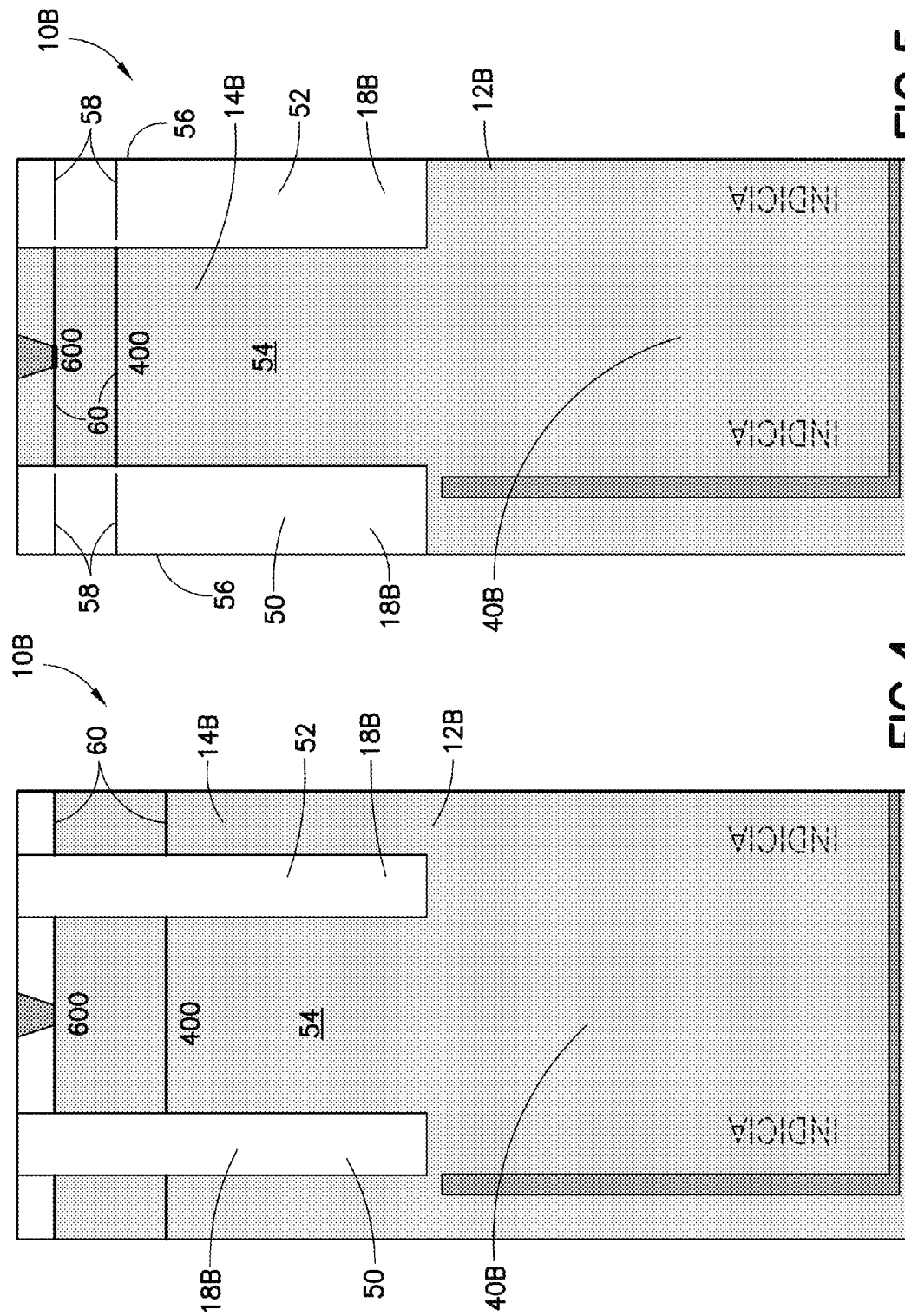

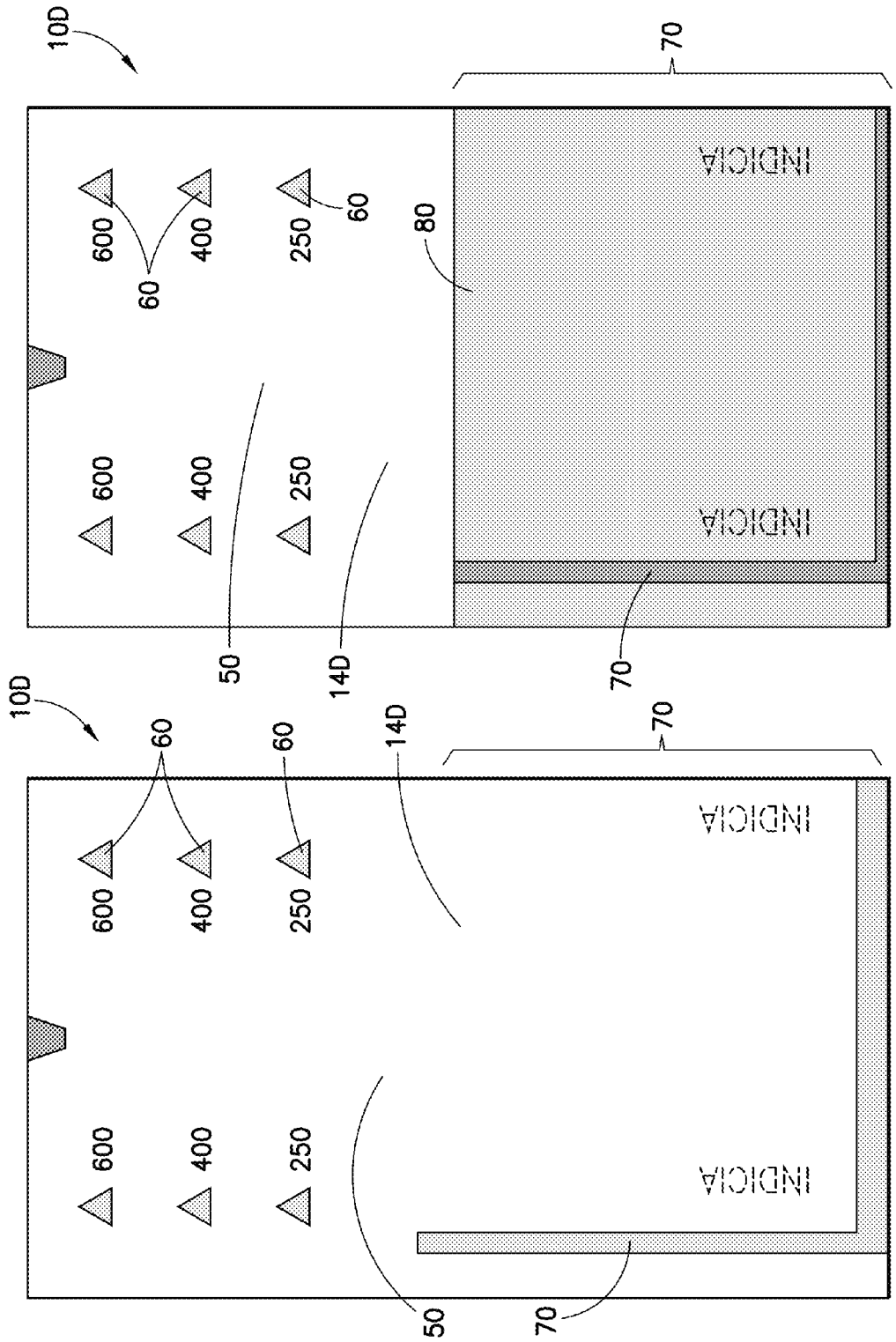

SPECIMEN CONTAINER LABEL FOR AUTOMATED CLINICAL LABORATORY PROCESSING SYSTEMS

CROSS-REFERENCE TO RELATED APPLICATION

This application claims priority to U.S. Provisional Patent Application No. 61/415,665, filed Nov. 19, 2010, entitled "Specimen Container Labeling for Automated Clinical Laboratory Processing Systems", the entire disclosure of which is herein incorporated by reference.

BACKGROUND OF THE INVENTION

1. Field of the Invention

The present invention relates to labels and labeling systems for use in connection with specimen collection containers. More specifically, the present invention relates to labels and labeling systems for specimen collection containers that do not interfere with conventional automated processing systems.

2. Description of Related Art

As part of automated clinical laboratory specimen processing, color-based image analysis is typically used to evaluate whether a sufficient volume of specimen is present within a specimen collection container to perform a specified diagnostic or evaluation testing procedure. Many testing procedures require a specified minimum volume of a biological sample in order for an accurate result to be determined. For example, in order for an accurate result to be determined from a typical blood sample, a minimum specimen level is required in order to perform most tests.

In order to determine whether a sample has a sufficient volume or specimen level, a color image of the specimen collection container housing the specimen is taken against a white or other colored background. If the image indicates that the volume of sample is sufficient to perform the test, then the specimen collection container is analyzed accordingly. If the image indicates that an insufficient volume is present within the specimen collection container, then the specimen collection container and contents are discarded.

Most specimen collection containers include at least one label disposed on the surface of the container. Labels typically include information pertaining to patient identification, collection dates, and/or the intended testing procedure to be performed on the sample. Labels typically interfere with the image capturing process for evaluating the volume of specimen housed within the specimen collection container because most systems cannot view the specimen volume through the label. Accordingly, some imaging systems may rotate the specimen collection containers to visualize a label-free window for the analysis. Imaging systems typically include an automated viewer operating with a red-green-blue (RGB) sensor to detect color variations and color levels correlating to specimen volumes. Any printing on the specimen collection container, including fill lines, lot numbers, or manufacturing logos can generate an error during specimen volume detection due to the color-based analysis of the contents of the specimen collection container. This is particularly true for any printing that may be covered by the backside of a label placed on the exterior surface of the specimen collection container.

Accordingly, a need remains for a label and labeling system for reducing the interference of labels, fill lines, lot numbers, manufacturing logos, and the like, which interfere with color-based imaging processes.

SUMMARY OF THE INVENTION

In accordance with an embodiment of the present invention, a label for application to a specimen collection container for automated viewing against a colored background is disclosed. The label includes a label body having a top surface and a bottom surface adapted for affixation to a specimen collection container, with the label body having a visualization window extending therethrough. The top surface includes printing thereon having a color substantially identical to a color of the background against which the label will be viewed.

The label may include a plurality of visualization windows extending between the top surface and the bottom surface. The label may also include additional printing disposed over the printing, with the additional printing having a second color, the second color being different from the color substantially identical to the color of the background. A flood coating may also be provided with the label, wherein the printing is disposed over the flood coating. In certain configurations, at least a portion of the label body is clear. In other configurations, at least a portion of the label body is white.

The label body may include at least one fill line. Optionally, the top surface of the label includes at least one fill line. In a further configuration, the visualization window includes at least one fill line, the fill line having a color substantially identical to the color of the background against which the label will be viewed. In still other configurations, a specimen collection container may be provided in contact with the bottom surface of the label body.

In accordance with another embodiment of the present invention, a label for application to a specimen collection container for automated viewing against a colored background is disclosed. The label includes a label body having a top surface having printing thereon, and a bottom surface adapted for affixation to a specimen collection container, the label body having a visualization window extending therethrough. The bottom surface has a color substantially identical to a color of the background against which the label will be viewed.

The label body may include at least one fill line. The top surface of the label may optionally include at least one fill line. In a further configuration, the visualization window may include at least one fill line, the fill line having a color substantially identical to the color of the background against which the label will be viewed. In still further configurations, a specimen collection container may be provided in contact with the bottom surface of the label body.

In accordance with yet another embodiment of the present invention, a specimen collection container for automated viewing against a colored background is disclosed. The specimen collection container includes an open top end, a closed bottom end, and a sidewall extending therebetween forming an interior adapted for receiving a specimen therein. The sidewall includes printing having a color substantially identical to a color of the background against which the specimen collection container will be viewed.

Optionally, the printing may include at least one fill line. The specimen collection container may also include a label disposed on a portion of the sidewall, with at least a portion of the label aligned with the sidewall including printing. The printing may include at least one fill line and the label may include at least one fill line aligned with the printing.

In accordance with yet another embodiment of the present invention, a specimen collection container for automated viewing against a colored background is disclosed. The specimen collection container includes an open top end, a closed bottom end, and a sidewall extending therebetween forming an interior adapted for receiving a specimen therein. The sidewall includes colorless indicia having a surface enhancement feature for providing visual distinction from at least a portion of the sidewall.

In certain configurations, the colorless indicia may include at least one fill line. The specimen collection container may also include a label disposed on a portion of the sidewall, with at least a portion of the label aligned with the sidewall including colorless indicia. The colorless indicia may include at least one fill line, and the label may include at least one fill line aligned with the colorless indicia.

In accordance with still a further embodiment of the present invention, a method for viewing a specimen within a specimen collection container is disclosed. The method includes providing a specimen collection container against a colored background. The specimen collection container includes an open top end, a closed bottom end, a sidewall extending therebetween forming an interior adapted for receiving a specimen therein, and a label having a label body disposed over at least a portion of the sidewall, in visual alignment with the colored background. At least one of the sidewall of the specimen collection container and the label body has printing disposed thereon having a color that is substantially identical to the colored background. The method also includes viewing the amount of specimen disposed within the interior of the specimen collection container.

Optionally, the sidewall of the specimen collection container includes printing that is substantially identical to the color of the colored background. The sidewall of the specimen collection container may include printing that is clear. In certain configurations, the printing includes at least one fill line. In other configurations, the label body is clear. The label body may include a top surface and a bottom surface adapted for affixation to a specimen collection container, with the label body having a visualization window extending therethrough. The top surface of the label body may include printing thereon having a color substantially identical to a color of the background against which the label will be viewed. The bottom surface may have a color substantially identical to a color of the background against which the label will be viewed. In further configurations, the method also includes determining whether there is sufficient specimen within the specimen collection container to perform an intended testing procedure. Optionally, viewing the amount of specimen disposed within the interior of the specimen collection container is performed by an automated viewing device.

In accordance with yet a further embodiment of the present invention, a method for viewing a specimen within a specimen collection container includes providing a specimen collection container against a colored background. The specimen collection container includes an open top end, a closed bottom end, a sidewall extending therebetween forming an interior adapted for receiving a specimen therein, and a label having a label body disposed over at least a portion of the sidewall, in visual alignment with the colored background. At least one of the sidewall of the specimen collection container and the label body includes colorless indicia having a surface enhancement feature for providing visual distinction from at least another portion of the sidewall or the label body. The method also includes viewing the amount of specimen disposed within the interior of the specimen collection container.

In certain configurations, the method also includes determining whether there is sufficient specimen within the specimen collection container to perform an intended testing procedure. In other configurations, viewing the amount of specimen disposed within the interior of the specimen collection container is performed by an automated viewing device.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 4 is a front view of a label having two visualization windows and fill lines in accordance with an embodiment of the present invention.

FIG. 5 is a front view of a label having two visualization windows and fill lines in accordance with an embodiment of the present invention.

FIG. 12 is a front view of a label having a visualization window and fill indicators in accordance with an embodiment of the present invention.

FIG. 13 is a front view of a label having a visualization window and fill indicators in accordance with an embodiment of the present invention.

DESCRIPTION OF PREFERRED EMBODIMENTS

For purposes of the description hereinafter, spatial orientation terms, if used, shall relate to the referenced embodiment, as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

The present invention is directed to a label, specimen collection container, and system for labeling in which any required printed information, such as any patient information, required tests, and/or fill lines, is not distinguishable from either the imaging background color or the underside color of the label. By structuring the printed information such that it is not distinguishable from either the imaging background color and/or the underside color of the label, automated imaging sensing systems do not detect the information, and thus the volumetric analysis may proceed without disruption or error.

Figure 1:
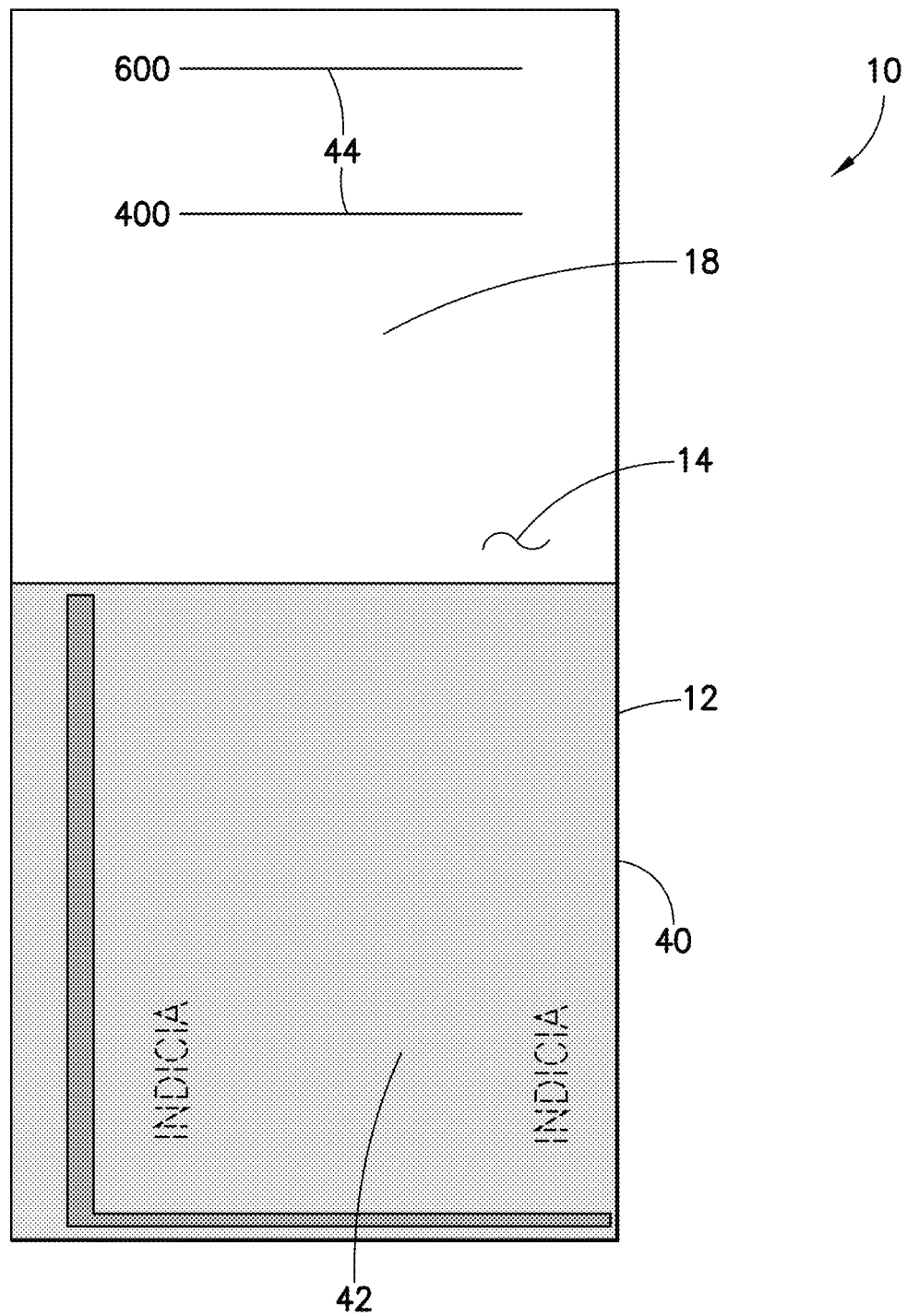
FIG. 1 is a front view of a label having a visualization window and fill lines in accordance with an embodiment of the present invention.
Figure 3:
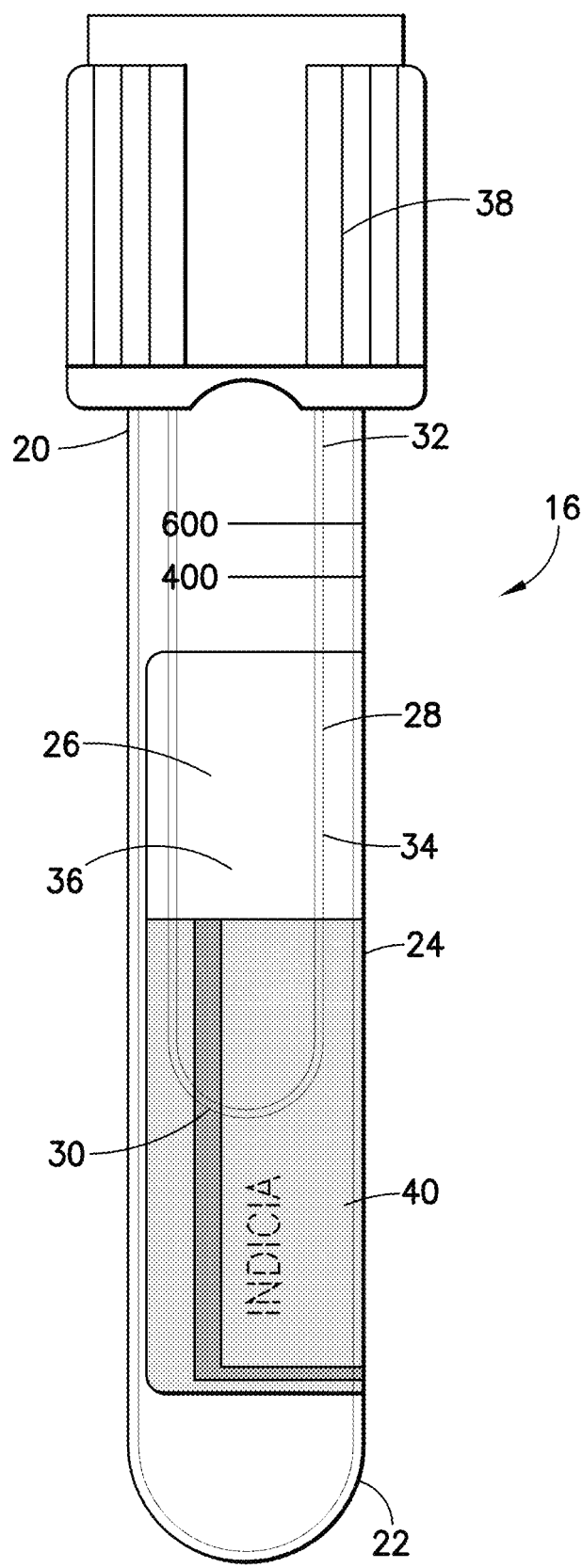
FIG. 3 is a front view of a specimen collection container having the label of FIG. 2 disposed thereon in accordance with an embodiment of the present invention.

With reference to FIG. 1, a label 10 may include a label body 12 having a top surface 14 and an opposing bottom surface (not shown) adapted for affixation to a specimen collection container 16, as shown in FIG. 3. In one embodiment, the bottom surface of the label 10 may include an adhesive for securement to the specimen collection container 16. The specimen collection container 16 may include an open top end 20, a closed bottom end 22, and a sidewall 24 extending therebetween, defining a container interior 26 adapted to receive a specimen, such as a biological specimen, such as blood, therein. In certain configurations, the specimen collection container 16 may be a single walled container formed of glass and/or a polymeric composition. In other configurations, as shown in FIG. 3, the specimen collection container 16 may include a tube-in-tube configuration in which a second specimen collection container 28 is disposed within the container interior 26. The second specimen collection container 28 may include a closed bottom end 30, an open top end 32, and a sidewall 34 extending therebetween defining a second container interior 36. The open top end 32 of the second specimen collection container 28 may be joined or otherwise secured with the open top end 20 of the specimen collection container 16, such that introduction of a specimen into the specimen collection container 16 also introduces the specimen into the second container interior 36. A closure 38 may cover the open top end 20 of the specimen collection container 16 and the open top end 32 of the second specimen collection container 28.

Referring again to FIG. 1, the label body 12 may include a visualization window 18 extending through the label body 12, such as extending from the top surface 14 to the bottom surface (not shown). When the label 10 is applied to a specimen collection container 16, as shown in FIG. 3, a specimen deposited within the container interior 26 and/or second container interior 36 may be visible through the visualization window 18. In certain embodiments, the visualization window 18 may be a cut-out portion of the label 10. In other embodiments, the visualization window 18 may be a clear portion of the label 10, such as a clear film portion. The label body 12 may also include an opaque region 40 on which indicia, such as patient identification, intended test identifiers, lot and batch information, tube specifications, and manufacturer information may be printed. Indicia printed on a top surface 42 of the opaque region 40 may include various colors.

The label body 12 may also include additional indicia 44 that is printed on a portion of the label 10 separate from the opaque region 40. This additional indicia 44 may include fill lines or other information pertaining to the specimen collection container and/or the contents therein. The additional indicia 44 may be printed on the label body 12, such as on the top surface 14 of the label body 12, in a color that is substantially identical to the color of the background against which the specimen collection container 16 will be analyzed by an automated viewer. Accordingly, if the specimen collection container 16 is analyzed against a white background to determine if sufficient volume of specimen is present within the specimen collection container 16 to perform a specified testing procedure, then white additional indicia 44 would be printed on the label body 12. Similarly, if the specimen collection container 16 is analyzed against a yellow background, then yellow additional indicia 44 would be printed on the label body 12. By substantially matching the color of the additional indicia 44 to the color of the background against which the specimen collection container 16 will be analyzed, the indicia is visible to a clinician during specimen collection but is not detected by the automated viewer during volumetric analysis. Accordingly, a clinician may be able to view a fill line printed in white on a label 10 disposed on a specimen collection container 16 during a blood draw, but the white fill line is not detected by the automated viewer and thus does not generate an error during the serum level analysis.

In certain embodiments, the opaque portion 40 may extend around only a portion of the sidewall 24 of the specimen collection container 16. Accordingly, in certain embodiments, the bottom surface (not shown) of the label body 12, specifically the bottom surface of the opaque portion 40, may have a color that is substantially identical to the color of the background against which the specimen collection container 16 is analyzed. Accordingly, if the specimen collection container 16 is analyzed against a white background, then the bottom surface of the opaque portion 40 of the label body 12 may also be white. In this configuration, the automated viewer would not be disrupted if the specimen collection container 16 was rotated such that the bottom surface of the label body 12 was positioned such that it would be provided in visual contact with the viewer through the opposing side of the specimen collection container 16, i.e., as seen through the back of the specimen collection container 16.

For purposes of illustration it is noted that throughout the present application, portions of the label 10 indicated as being clear are shown in the accompanying figures as being white in color, and that portions of the label 10 indicated as being white are shown in the accompanying figures in grey scale. Accordingly, with reference to FIG. 1 for example, the opaque portion 40 is shown as having a white background, whereas the visualization window 18 is shown as being clear. Similarly, the additional indicia 44 is shown as being white in color as printed on the clear visualization window 18.

Figure 2:
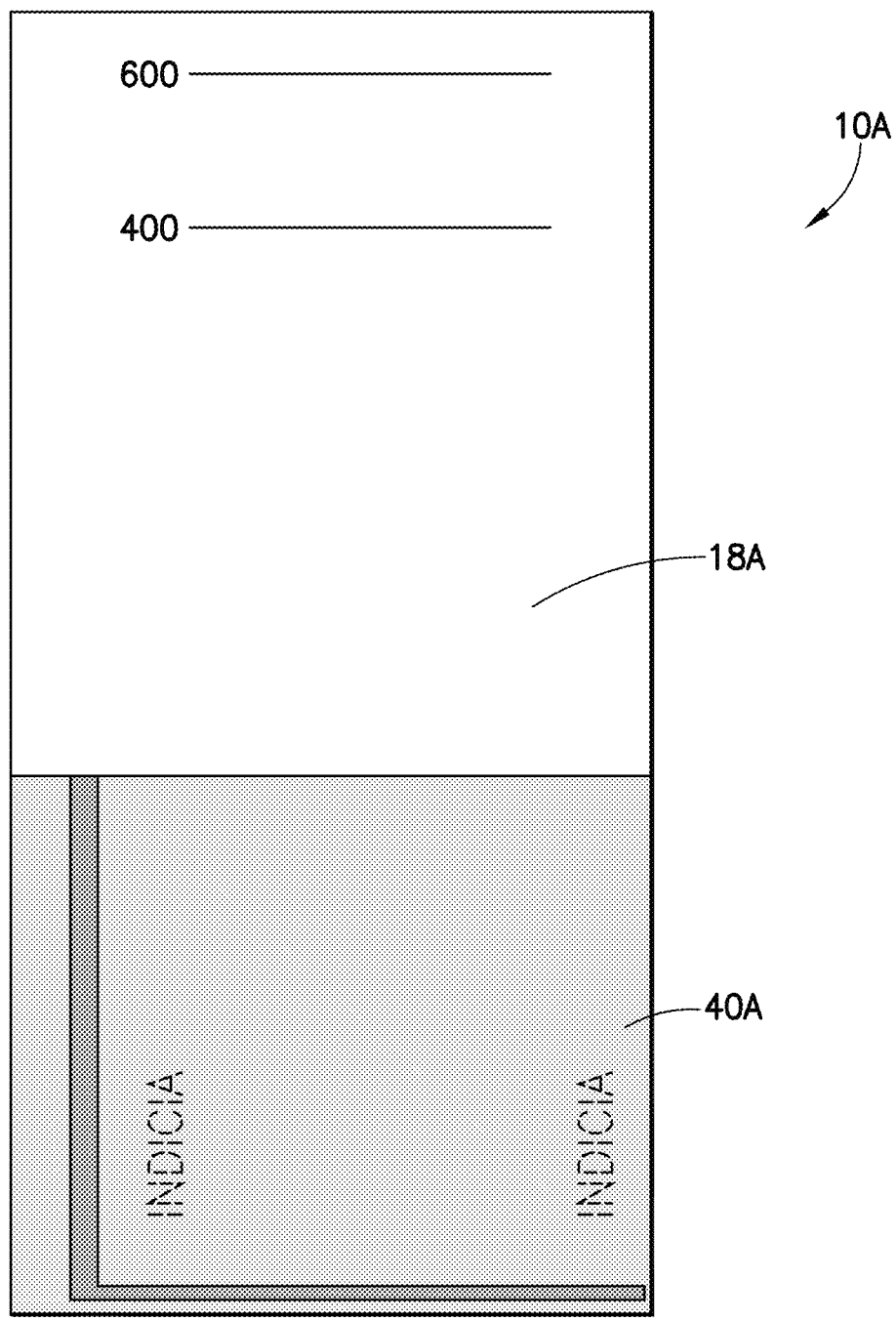
FIG. 2 is a front view of a label having an extended visualization window and fill lines in accordance with an embodiment of the present invention.

Referring to FIG. 2, in certain situations a label 10A having an enlarged visualization window 18A may be desirable. This may be particularly true during a small volume blood draw in which the clinician desires to visualize an enlarged viewing area of the contents of the specimen collection container 16. Accordingly, in this configuration, the relative proportioning of an opaque portion 40A and the visualization window 18A may be adjusted to provide a reduced area opaque portion 40A and an increased area visualization window 18A. As shown in FIGS. 1-3, at least a portion of the label body 12 may be clear. In other situations, it may be desired that the entire label body 12 may be clear, with additional printing indicia 44 having a color substantially identical to the color of the background against which the tube will be viewed. In another configuration, at least a portion of the label body 12 may be white. In other situations, it may be desired that the entire label body 12 be white, with additional printing indicia 44 having a color substantially identical to the color of the background against which the tube will be viewed.

Figure 6:
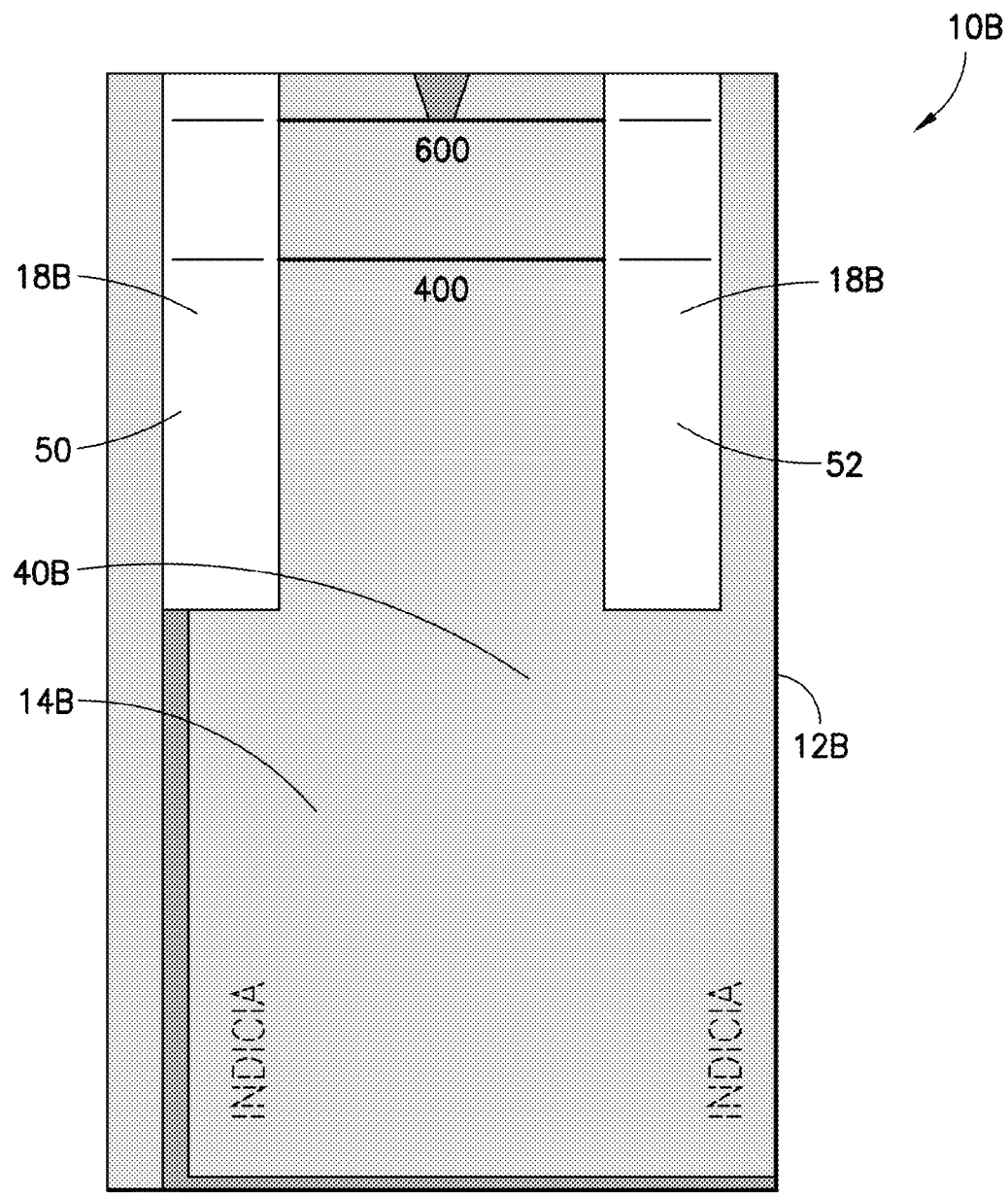
FIG. 6 is a front view of a label having two visualization windows and fill lines in accordance with an embodiment of the present invention.
Figure 7:
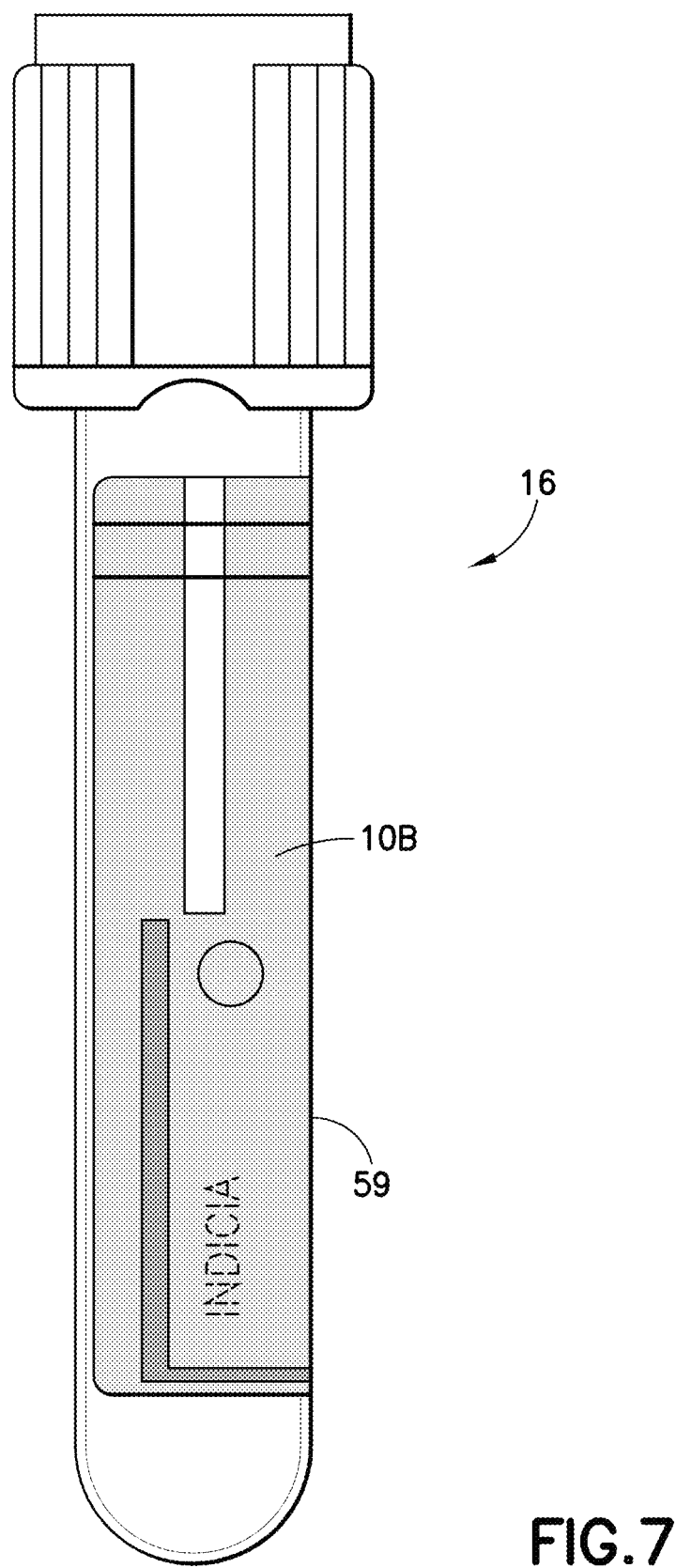
FIG. 7 is a front view of a specimen collection container having the label of FIG. 4 disposed thereon in accordance with an embodiment of the present invention.
Figure 9:
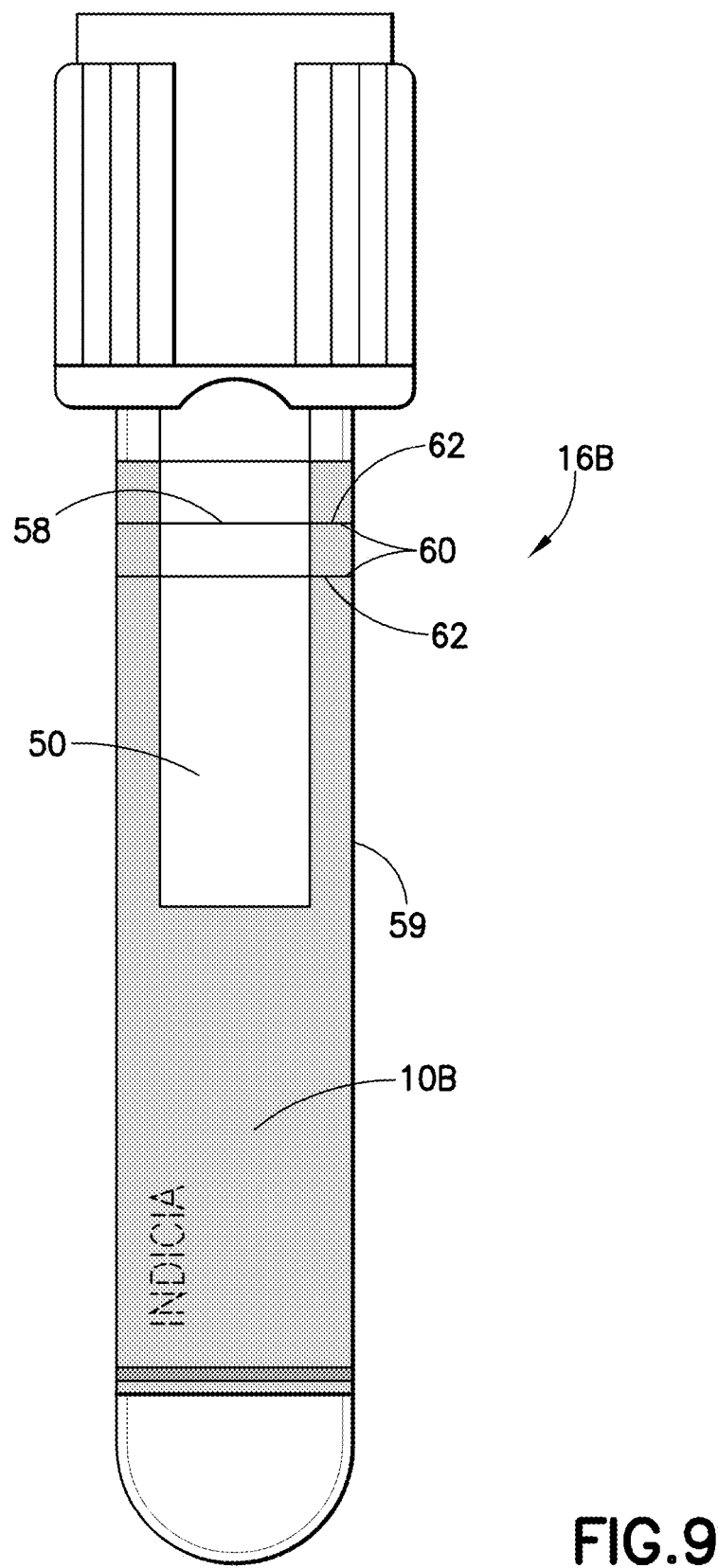
FIG. 9 is a front view of a specimen collection container having the label of FIG. 8 disposed thereon in accordance with an embodiment of the present invention.

Referring to FIGS. 4-6, in certain configurations a label body 12B of a label 10B may include a plurality of visualization windows 18B, such as a first visualization window 50 and a second visualization window 52 extending between a top surface 14B and the bottom surface (not shown) opposing the top surface 14B. As shown in FIG. 4, the first visualization window 50 and the second visualization window 52 may be disposed within an opaque portion 40B. In another configuration, the first visualization window 50 and the second visualization window 52 may be oriented in a substantially vertical orientation such that when the label body 12B is positioned on a specimen collection container 16B, as shown in FIG. 9, a clinician may view the amount of specimen being deposited within the specimen collection container 16B during specimen draw, and an automated viewer may determine the volume of specimen present within the specimen collection container 16B for subsequent analysis.

Referring again to FIG. 4, in one embodiment, the label body 12B may include a first visualization window 50 and a second visualization window 52 disposed within the interior region of the label body 12B, such as within an interior region 54. The label body 12B may also include other indicia 60, such as fill lines, printed on the top surface 14B. As shown in FIG. 4, the fill lines or other indicia 60 may be provided adjacent the first visualization window 50 and/or the second visualization window 52 to enable a clinician to easily view the amount of sample being introduced into the specimen collection container 16B during specimen draw.

In certain situations, the automated viewer may require a label-free area for performing specimen volume analysis, and will rotate the specimen collection container in search of a viewable area. Accordingly, it may be necessary to dimension and position the visualization window 50 such that the automated viewer does not mistake the visualization window 50 for a label-free area, which may be defined as the gap between leading and trailing edges of the label. For example, for testing performed on standard specimen collection containers having an outer diameter of from 10-16 mm and an overall height of from 75-100 mm, the minimum required label-free area for volume analysis may be 6.5 mm and must extend the entire length or height of the specimen collection container. Accordingly, in one embodiment, the visualization window 50 may have a length that is less than 6.5 mm and have a height that is less than the height of the overall label.

Referring to FIG. 5, in accordance with another embodiment, the label body 12B may include a first visualization window 50 and a second visualization window 52 disposed adjacent a perimeter 56 of the label body 12B. In certain configurations, the label body 12B may include other indicia 60, such as fill lines, printed on the top surface 14B. As previously described herein, the label body 12B may be affixed to a specimen collection container 16B. Optionally, at least one of the first visualization window 50 and the second visualization window 52 include additional indicia 58 having the same color as the background color against which the specimen collection container 16B will be viewed. In certain configurations, the additional indicia 58 disposed on or within the first and/or second visualization windows 50, 52 may be at least partially aligned with the other indicia 60 present on the label body 12B. In this embodiment, the other indicia 60 present on the label body 12B may be of any color, whereas the additional indicia 58 present on the first visualization window 50 and/or the second visualization window 52 has the same color as the background color against which the specimen collection container 16B will be viewed.

The labels 10, 10A, 10B of the present invention may be disposed on a wide variety of specimen collection containers 16, 16B. Accordingly, the size of the label may be adjusted accordingly to accommodate either larger or smaller specimen collection container exterior surface areas. As shown in FIG. 6, a widened label 10B may be provided such that when applied to the surface of the specimen collection container 16B, as shown in FIG. 9, the label 10B may cover a portion of an exterior surface 59 of the specimen collection container 16B extending up to about 270° of the circular perimeter of the specimen collection container 16B. In one embodiment, the label 10B may cover any suitable portion of the exterior surface 59 of the specimen collection container 16B, such as from about 180° extending up to about 360° of the circular perimeter of the specimen collection container 16B.

Figure 8:
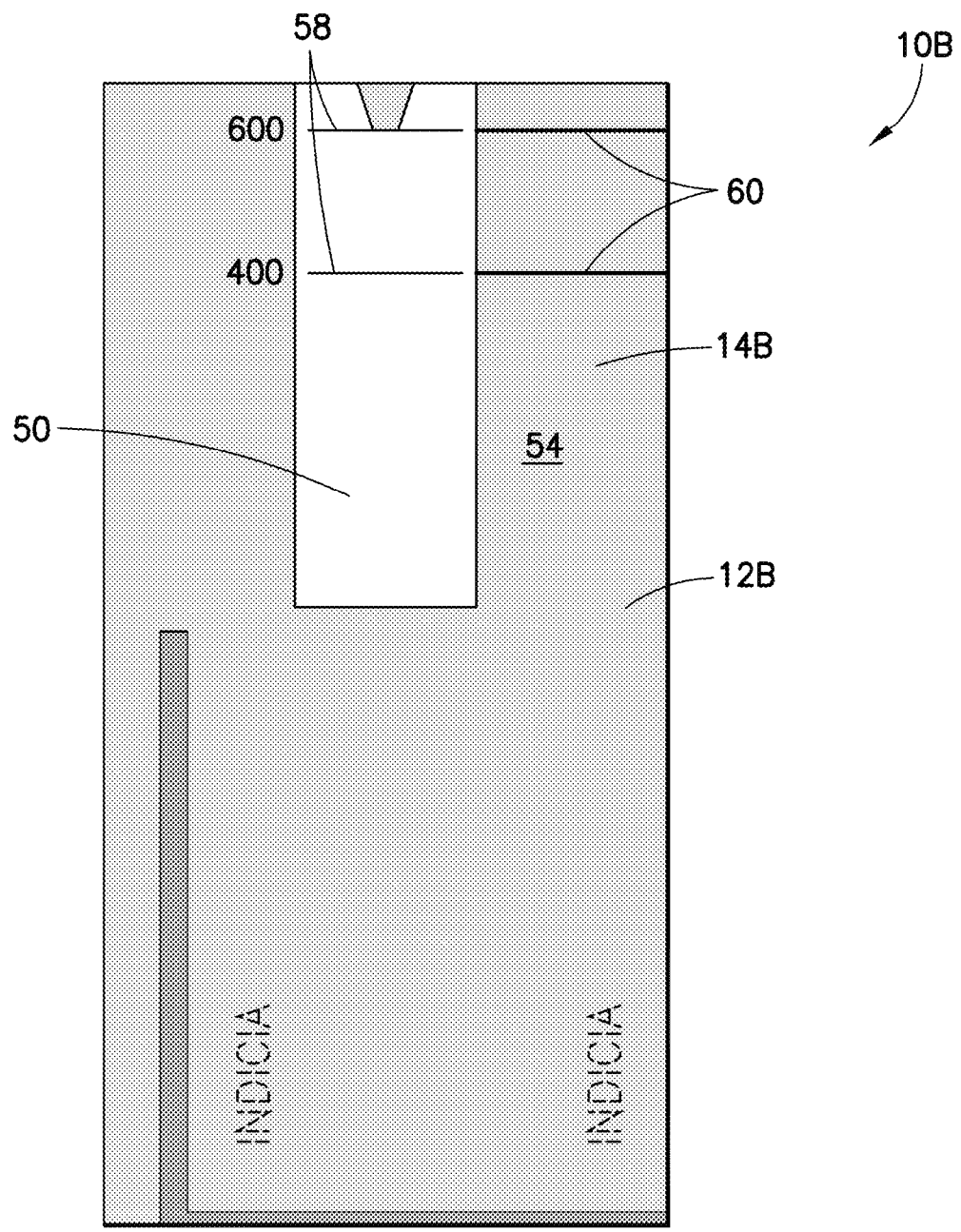
FIG. 8 is a front view of a label having a visualization window and fill lines in accordance with an embodiment of the present invention.

Referring to FIGS. 8-9, in certain configurations, a single visualization window 50 may be disposed within the interior region of the label body 12B, such as within the interior region 54. As described hereinabove, the top surface 14B of the label body 12B may include a printed other indicia 60 and/or additional indicia 58 disposed within or on the visualization window 50. When the label 10B is applied to the exterior surface 59 of the specimen collection container 16B, at least a portion of the other indicia 60, such as fill lines, printed on the top surface 14B of the label body 12B and/or the additional indicia 58 disposed on or within the visualization window 50, may be aligned with a printing 62, such as a fill line, disposed on the specimen collection container 16B. In certain situations, at least a portion of the other indicia 60 and/or the additional indicia 58 may cover a portion of the fill line 62 of the specimen collection container 16B.

Figure 10:
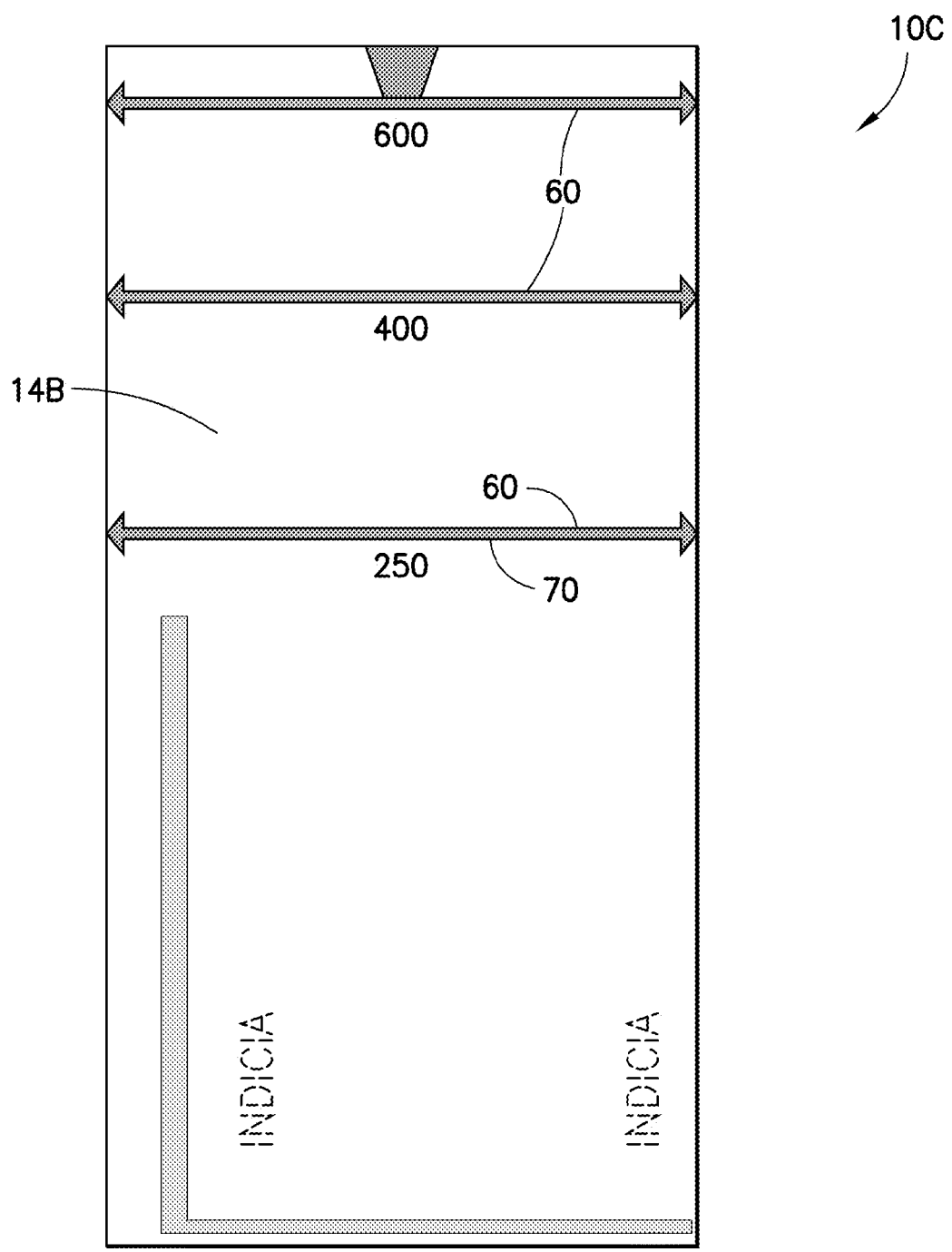
FIG. 10 is a front view of a label having a flood coating and fill lines in accordance with an embodiment of the present invention.
Figure 11:
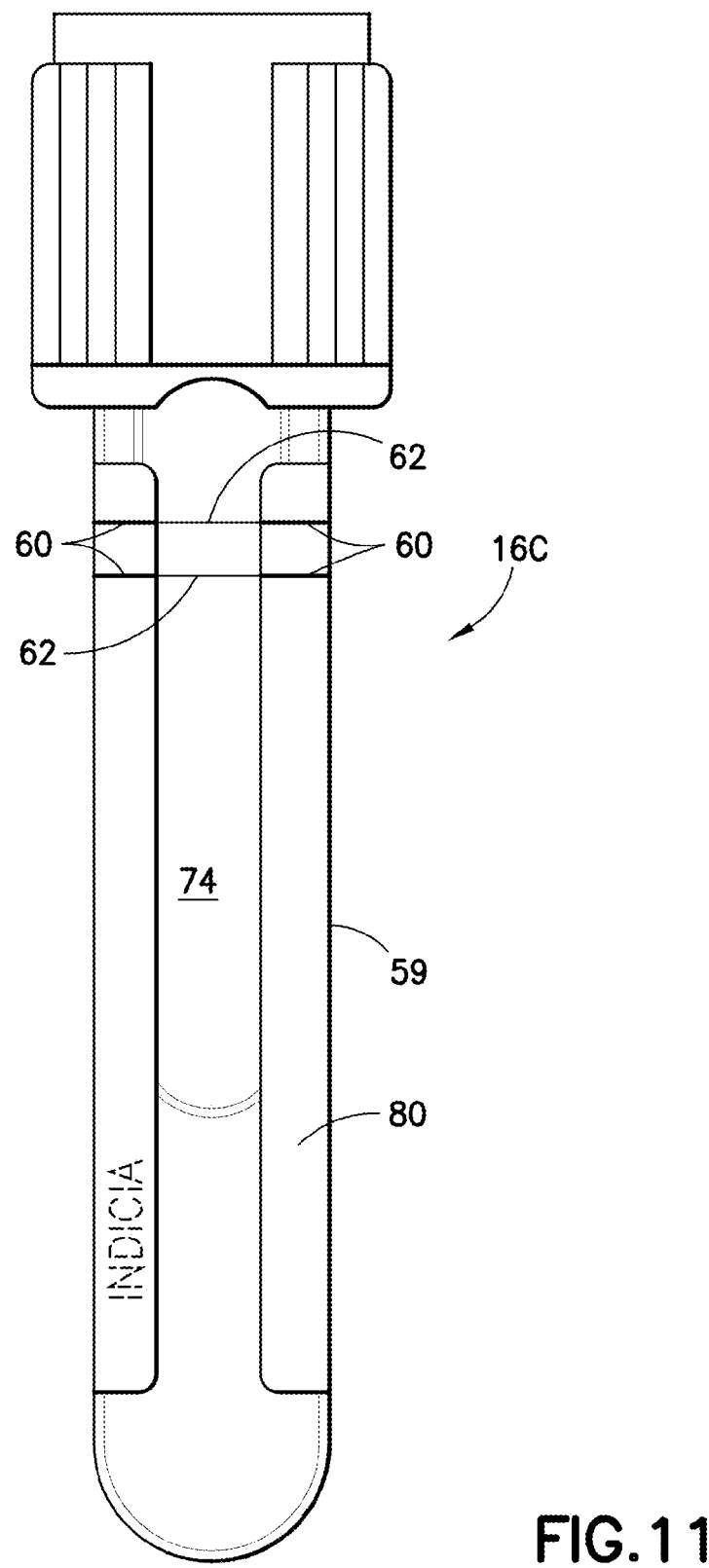
FIG. 11 is a front view of a specimen collection container having the label of FIG. 10 disposed thereon in accordance with an embodiment of the present invention.

Referring to FIGS. 10-11, in one embodiment, the label 10C includes other indicia 60 or printing having a color substantially identical to a color of the background against which the label will be viewed, as previously discussed herein. In certain situations, however, it may be desirable to provide indicia 60 or other printing that has a color different from the background color, yet does not create the errors in visual analysis as previously discussed. In these situations, the indicia 60 may include additional printing 70 disposed over the indicia 60 that has a color that is different from the color of the background. For example, if a specimen collection container 16C having a label 10C disposed thereon is to be viewed against a white background, then the other indicia 60 may be initially printed on the label 10C and/or specimen collection container 16C in white. Subsequently, a printing 70 having a second color, such as black, may be printed over the indicia 60. Accordingly, when the label 10C of the specimen collection container 16C is viewed from the front, such as looking directly at the label 10C disposed on the exterior surface of the specimen collection container 16C, then the black printing is visible. When the label 10C of the specimen collection container 16C is viewed from the back or bottom surface, such as when the interior surface of the tube is viewed through either a visualization window, as discussed above, or a portion of a tube 74 that is not covered by the label 10C, then the white printing is visible. Accordingly, in this configuration, the clinician may have the benefit of viewing easily discernable black print, whereas the automated viewer visualizes the white print and does not process the black print disposed thereover.

In another configuration, a flood coating 80 of a first color that is substantially identical to the background color against which the specimen collection container 16C will be viewed may be provided over at least a portion of the label 10C and/or the specimen collection container 16C. The flood coating 80 may be printed over a larger region of the label 10C and/or specimen collection container 16C than the indicia 60. In this configuration, a printing 70, having a second color that is different from the background color may be printed over the flood coating 80 in a similar manner as described above. A benefit of utilizing a flood coating 80 is that the alignment of the printing 70 does not need to be as precise as when the printing 70 is disposed over other indicia 60. For example, if a white fill line having a 1 mm thickness is printed on a clear label as indicia 60, and a 1 mm black fill line printing 70 is printed over the white fill line indicia 60, then the alignment between the indicia 60 and the printing 70 must be perfect in order to prevent inadvertent portions of the printing 70 to be visible from the bottom surface of the label 10C and viewable by an automated viewer. Accordingly, the thickness of the printing 70 may be reduced, or a larger flood coating 80 may be deposited over the label 10C and/or specimen collection container 16C to increase the printing tolerance.

Referring again to FIGS. 10-11, when the label 10C is applied to the exterior surface 59 of the specimen collection container 16C, at least a portion of the other indicia 60 printed on the top surface 14B of the label 10C, and/or the additional indicia 58 disposed on or within the visualization window 50, as shown in FIGS. 8-9, may be aligned with a printing 62. Printing 62 may include a fill line, disposed on the specimen collection container 16C. In certain situations, at least a portion of the other indicia 60 and/or the additional indicia 58 may cover a portion of the printing 62 of the specimen collection container 16C. The printing 62 on the specimen collection container 16C may have a color that is substantially identical to the color of the background against which the specimen collection container will be viewed. As shown in FIG. 11, the printing 62 may include one or more fill lines.

Referring to FIGS. 12-13, alternative labels 10D are shown in which the other indicia 60 may include fill indicators and volumetric representations. FIG. 12 illustrates the other indicia 60 printed within the visualization window 50 in a color that is substantially identical to the background color against a specimen collection container to which the label 10D would be applied would be viewed. Additional printing 70 in various colors that are different from the background color are shown printed over corresponding indicia 60 such that the additional printing 70 in the various colors is visible only from a top surface 14D of the label 10D. Similarly, FIG. 13 illustrates the identical label with the additional printing 70 in various colors that are different from the background color shown printed over a flood coating 80 having the same color as the background color.

Figure 14:
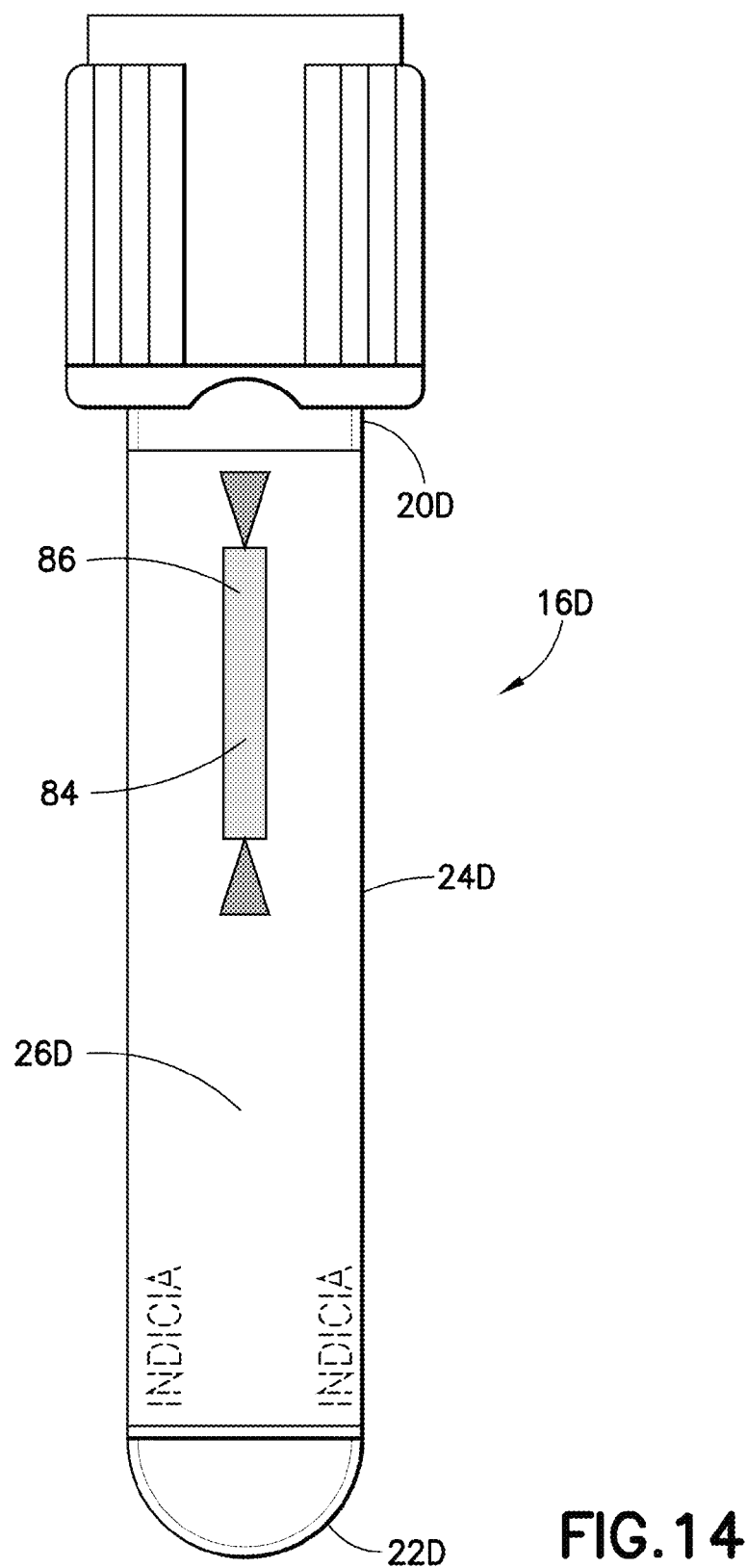
FIG. 14 is a front view of a specimen collection container having a physical fill line and a label disposed thereover in accordance with an embodiment of the present invention.

Referring to FIG. 14, a specimen collection container 16D for automated viewing against a colored background includes an open top end 20D, a closed bottom end 22D, and a sidewall 24D extending therebetween forming an interior 26D adapted for receiving a specimen therein. The specimen collection container 16D may include printing on the sidewall 24D, such as disposed on an exterior surface of the sidewall 24D or disposed within a portion of the sidewall 24D. As described above, the printing may be of a color that is substantially identical to the color of a background against which the specimen collection container 16D is viewed. The printing may include a fill line indicator and/or identifying indicia, as described above.

Referring again to FIG. 14, the sidewall 24D of the specimen collection container 16D may include colorless indicia 84 having a surface enhancement feature 86 for providing visual distinction from at least a portion of the sidewall 24D. The surface enhancement feature 86 may be provided by etching, knurling, or in-molding the colorless indicia 84 into the specimen collection container 16D. In a further embodiment, the surface enhancement feature 86 provides a difference in surface texture to create a visual distinction between the colorless indicia 84 and the sidewall 24D of the specimen collection container 16D. In a further embodiment, the colorless indicia may include at least one fill line. The colorless indicia 84 may be provided in any orientation, such as substantially vertical or substantially horizontal. The colorless indicia may extend up to a full or partial length or circumference of the specimen collection container 16D.

Figure 15:
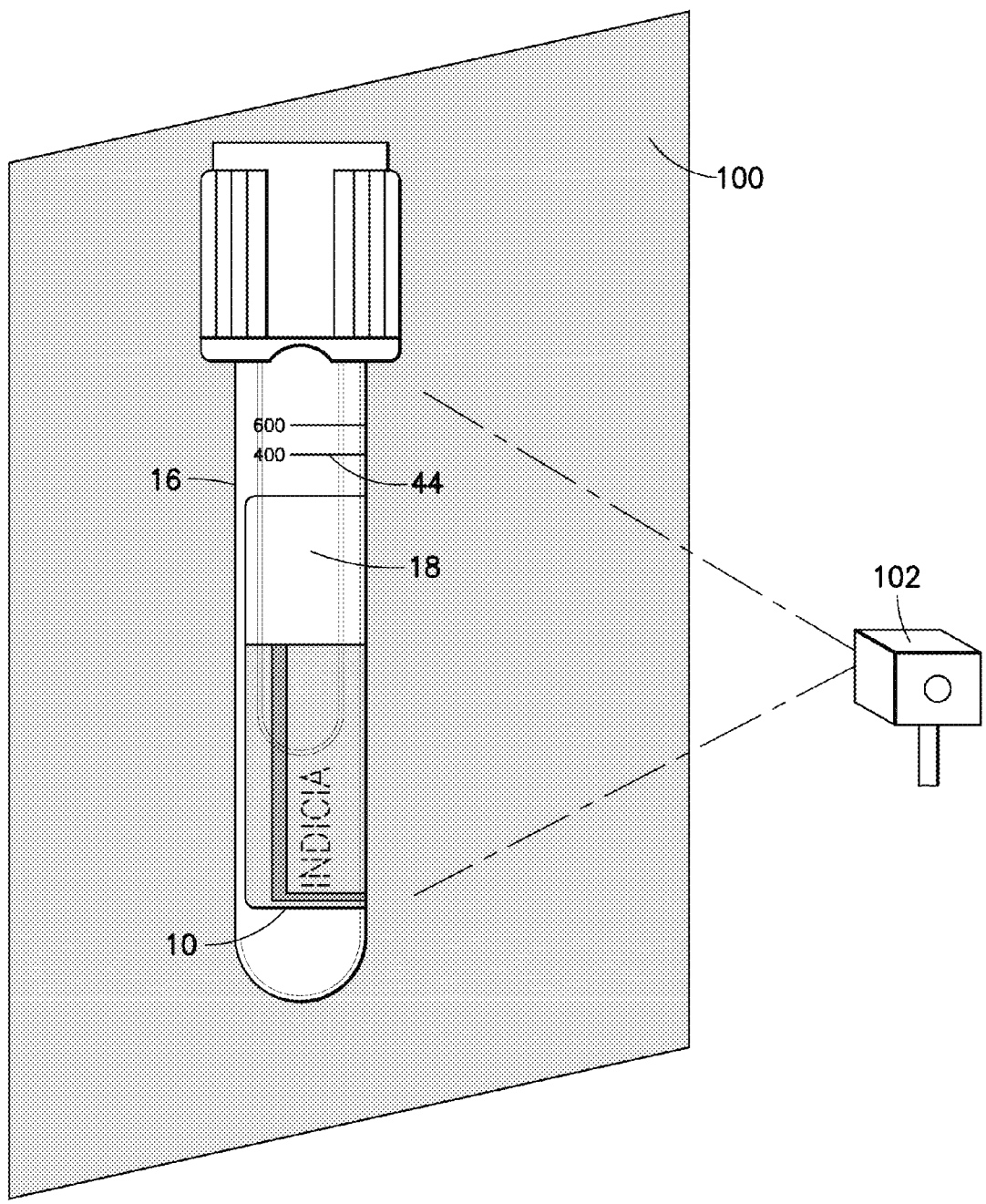
FIG. 15 is a perspective schematic view of a system for viewing a specimen collection container having a label disposed thereon against a colored background in accordance with an embodiment of the present invention.

Referring to FIG. 15, a specimen collection container 16 having a label 10 disposed thereon and having a biological specimen disposed therein is provided against a colored background 100. The specimen collection container 16 is aligned with a camera or other electronic eye 102 which allows the specimen collection container 16 to be analyzed by the electronic eye 102. The electronic eye 102 determines whether there is sufficient volume of specimen disposed within the specimen collection container 16 to perform an intended testing procedure. The electronic eye 102 may view the sufficiency of the specimen within the specimen collection container 16 by reference to indicia 44, such as a fill line. The electronic eye 102 may also view the sufficiency of the specimen within the specimen collection container 16 through the visualization window 18. As described herein, the indicia 44 and the background 100 have substantially the same color so as not to permit the indicia 44 to interfere with the electronic eye 102. In a further embodiment, the indicia 44 is colorless and has a surface enhancement feature 86 for providing visual distinction from at least another portion of the specimen collection container 16. In this system, analyzing the volume of the contents of the specimen collection container 16 by the electronic eye 102 includes determining whether there is sufficient specimen within the specimen collection container to perform an intended testing procedure.

In certain configurations, the provision of the specimen collection container 16 having a biological sample disposed therein against the colored background 100, and the analyzing of the volume of the contents of the specimen collection container 16 may be partially or fully automated. If the image indicates that the volume of sample is sufficient to perform the test, then the specimen collection container is analyzed accordingly. If the image indicates that an insufficient volume is present within the specimen collection container, then the specimen collection container and contents are discarded.

While several embodiments of a label, a specimen collection container, and an automated process for analyzing the volume of a specimen collection container have been described in the foregoing detailed description, those skilled in the art may make modifications and alterations to these embodiments without departing from the scope and spirit of the invention. Accordingly, the foregoing description is intended to be illustrative rather than restrictive.

What is claimed is:

1. A system for application of a label to a specimen collection container for automated viewing against a colored background, comprising:
   the colored background; and
   the label comprising a label body having a top surface and a bottom surface adapted for affixation to the specimen collection container, the label body having a visualization window defined therethrough,
   wherein the top surface includes printing thereon having a color substantially identical to a color of the entire colored background against which the label is viewed during the automated viewing, and wherein the colored background is external to the specimen collection container.

2. The system of claim 1, wherein the label has a plurality of visualization windows defined between the top surface and the bottom surface.

3. The system of claim 1, wherein the label includes additional printing disposed over the printing, the additional printing having a second color, the second color being different from the color substantially identical to the color of the colored background.

4. The system of claim 1, wherein the label further comprises a flood coating, and wherein the printing is disposed over the flood coating.

5. The system of claim 1, wherein at least a portion of the label body is clear.

6. The system of claim 1, wherein at least a portion of the label body is white.

7. The system of claim 1, wherein the label body comprises at least one fill line.

8. The system of claim 7, wherein the top surface of the label includes the at least one fill line.

9. The system of claim 1, wherein the visualization window includes at least one fill line, the fill line having a fill line color substantially identical to the color of the colored background against which the label is viewed.

10. The system of claim 1, wherein the label further comprises the specimen collection container in contact with the bottom surface of the label body.

11. A system for application of a label to a specimen collection container for automated viewing against a colored background, comprising:
the colored background; and
the label comprising a label body having a top surface having printing thereon, and a bottom surface adapted for affixation to the specimen collection container, the label body having a visualization window defined therethrough,
wherein the bottom surface has a color substantially identical to a color of the entire colored background against which the label is viewed during the automated viewing, and wherein the colored background is external to the specimen collection container.

12. The system of claim 11, wherein the label body comprises at least one fill line.

13. The system of claim 11, wherein the top surface of the label includes at least one fill line.

14. The system of claim 11, wherein the visualization window includes at least one fill line, the fill line having a fill line color substantially identical to the color of the colored background against which the label is viewed.

15. The system of claim 11, wherein the label further comprises the specimen collection container in contact with the bottom surface of the label body.

16. A system for automated viewing of a specimen collection container against a colored background, comprising:
the colored background; and
the specimen collection container comprising:
an open top end;
a closed bottom end; and
a sidewall extending therebetween forming an interior adapted for receiving a specimen therein,
wherein the sidewall includes printing having a color substantially identical to a color of the entire colored background against which the specimen collection container is viewed during the automated viewing, and wherein the colored background is external to the specimen collection container.

17. The system of claim 16, wherein the printing comprises at least one fill line.

18. The system of claim 16, wherein the specimen collection container further comprises a label disposed on a portion of the sidewall, at least a portion of the label aligned with the sidewall including printing.

19. The system of claim 18, wherein the printing comprises at least one fill line and the label comprises at least one fill line aligned with the printing.

20. A method for viewing a specimen within a specimen collection container, comprising:
providing a specimen collection container against a colored background, the specimen collection container comprising:
an open top end;
a closed bottom end;
a sidewall extending therebetween forming an interior adapted for receiving the specimen therein; and
a label having a label body disposed over at least a portion of the sidewall, in visual alignment with the colored background, wherein at least one of the sidewall of the specimen collection container and the label body have printing disposed thereon having a color that is substantially identical to the entire colored background, and wherein the colored background is external to the specimen collection container; and
viewing, from a side facing the printing, the amount of specimen disposed within the interior of the specimen collection container.

21. The method of claim 20, wherein the sidewall of the specimen collection container includes printing that is substantially identical to the color of the colored background.

22. The method of claim 20, wherein the sidewall of the specimen collection container includes printing that is clear.

23. The method of claim 20, wherein the printing includes at least one fill line.

24. The method of claim 20, wherein the label body is clear.

25. The method of claim 20, wherein the label body includes a top surface and a bottom surface adapted for affixation to the specimen collection container, the label body having a visualization window defined therethrough.

26. The method of claim 25, wherein the top surface includes printing thereon having a color substantially identical to a color of the colored background against which the label is viewed.

27. The method of claim 25, wherein the bottom surface has a color substantially identical to a color of the colored background against which the label is viewed.

28. The method of claim 20, further comprising determining whether there is sufficient specimen within the specimen collection container to perform an intended testing procedure.

29. The method of claim 20, wherein viewing the amount of specimen disposed within the interior of the specimen collection container is performed by an automated viewing device.

* * * * *